United States Patent [19]

Bridger

[11] 4,208,292

[45] Jun. 17, 1980

[54] PHOSPHOMOLYBDATE COMPOUNDS AND THEIR USE AS LUBRICANT ADDITIVES

[75] Inventor: Robert F. Bridger, Hopewell, N.J.

[73] Assignee: Mobil Oil Corporation, New York, N.Y.

[21] Appl. No.: 7,057

[22] Filed: Jan. 29, 1979

[51] Int. Cl.² .................. C10M 1/48; C10M 3/42; C10M 5/24; C10M 7/46
[52] U.S. Cl. ....................... 252/32.7 E; 260/429 R
[58] Field of Search ............... 260/429 R; 252/32.7 E

[56] References Cited

U.S. PATENT DOCUMENTS

| | | | |
|---|---|---|---|
| 3,356,702 | 12/1967 | Farmer et al. | 260/429 R |
| 3,400,140 | 9/1968 | Rowan et al. | 260/429 R |
| 3,402,188 | 9/1968 | Wiese | 260/429 R |
| 3,419,589 | 12/1968 | Larson et al. | 260/429 R |
| 3,840,463 | 10/1974 | Froeschmann et al. | 252/32.7 E X |
| 3,888,776 | 6/1975 | Silverstein | 252/32.7 E X |
| 4,098,705 | 7/1978 | Sakurai et al. | 260/429 R X |

Primary Examiner—Helen M. S. Sneed
Attorney, Agent, or Firm—Charles A. Huggett; Raymond W. Barclay; Claude E. Setliff

[57] ABSTRACT

The invention provides a phosphomolybdate compound that is useful in lubricants, especially lubricating oils, to reduce friction and to decrease fuel consumption in internal combustion engines. The phosphomolybdates are new compounds obtained at or near room temperature.

26 Claims, No Drawings

PHOSPHOMOLYBDATE COMPOUNDS AND THEIR USE AS LUBRICANT ADDITIVES

BACKGROUND OF THE INVENTION

1. Field of the Invention

The invention relates, in one aspect, to a method for reducing fuel consumption in internal combustion engines. It more particularly relates to reducing fuel consumption by adding a phosphomolybdate to the lubricating oil used.

2. Discussion of the Prior Art

For several years there have been numerous efforts to reduce the amount of fuel consumed by automobile engines and the like. The search for ways to do this was given added impetus by the oil embargo. Many of the solutions have been strictly mechanical, as for example, setting the engine for a leaner burn or simply building smaller cars and smaller engines.

Other efforts have revolved around finding lubricants that reduce the overall friction in the engine, thus allowing a reduction in energy requirements thereto. On the one hand, a considerable amount of work has been done with mineral lubricating oils and greases, modifying them with additives to enhance their friction properties. On the other hand, new lubricants have been synthesized and compounded for use in modern engines. Among these is Mobil 1, a synthetic hydrocarbon fluid and synthetic ester blend, which is known to reduce fuel consumption by a significant amount. It is, however, the physical properties of the oil itself that provide improved lubrication (and thus improved fuel consumption) and not the additives present.

U.S. Pat. No. 3,400,140 discloses the use of phosphomolybdates, but as will appear hereinafter, the compounds of the present invention are neither taught nor suggested by this patent. So far as is known, they are not taught or suggested by any reference or combination of references.

SUMMARY OF THE INVENTION

In accordance with the invention, there is provided a compound having the formula:

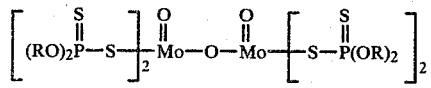

wherein R may be the same or different and is a $C_3$–$C_{30}$ hydrocarbyl group. The invention also provides lubricant compositions containing the compound and a method for reducing fuel consumption in an internal combustion engine by treating the moving surfaces thereof with the said composition.

DESCRIPTION OF SPECIFIC EMBODIMENTS

It has been estimated that a modern car weighing about 4300 pounds with a 10:1 compression ratio and travelling at 40 mph on a level roadway has available for propelling it only 13.1% of the energy available in the gasoline burned. The losses are due primarily to fuel pumping, tare, friction, transmission, rear axle, tires, and wind resistance. The actual fuel used in propelling the vehicle amounted to 16.7 mpg. If all fuel were used in propelling the vehicle, it could travel 128 miles on a gallon of gasoline.

Of the energy loss, approximately 5%, or 6.4 mpg. can be accounted for in loss due to lubricating engine components. Consequently, a mere 10% decrease in boundary and viscous friction would lead to a 3.8% increase in fuel economy (from 16.7 mpg. to 17.3 mpg.). It is little wonder, then, that energy companies are concerned with finding new lubricants or new additives that have superior lubricity properties.

As was mentioned hereinabove, one method of boosting fuel economy is to optimize the lubrication of the engine and drive train; that is, minimize friction losses between lubricated moving parts. The benefit of Mobil 1 over, for example, Mobil Super is better than 4%, attained solely by lowering of the viscous friction of the engine lubricant. Additional improvements may be realized by modification of the boundary friction of the lubricant.

In this invention, the compounds may be prepared by reacting a metal molybdate, e.g. an alkali metal molybdate, or an ammonium molybdate, such as ammonium hexamolybdate, with a dihydrocarbyl phosphorodithioic acid. The molybdate can be formed by dissolving molybdic oxide in a solution of alkali metal hydroxide or another hydroxide of magnesium, beryllium or the like, or in a solution of ammonium hydroxide.

The dihydrocarbyl phosphorodithioic acid can be prepared in accordance with prior art methods by reacting monohydric alcohol with phosphorus pentasulfide to obtain a product of the formula:

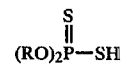

wherein R is defined as hereinabove, i.e. a $C_3$–$C_{30}$ hydrocarbyl group. "Hydrocarbyl" herein means alkyl, cycloalkyl, aryl or alkaryl. When R is alkyl, the preferred number of carbon atoms is from 3 to 20, preferably 4 to 14. When R is aryl, it may contain from 6 to 14 carbon atoms. The alkyl group in "alkaryl" will be selected such that the total carbon atoms in the aryl and the alkyl portions together will never exceed 30. That is, if the aryl portion is phenyl or naphthyl then the alkyl portion can have up to 24 or 20 carbon atoms, respectively.

It is essential to the successful synthesis of meaningful amounts of the product of this invention that a temperature below 85° C. be used. This is for the reason that U.S. Pat. No. 3,400,140 discloses that the product

[(RO)$_2$PS—S]$_2$Mo$_2$S$_2$O$_2$ is obtained at from 85° C. to 100° C. On the other hand, it has been found that temperatures up to 80° C. yield substantial amounts of the product of this invention. The following table shows this

TABLE 1

| Temp., °C. | % Product |
|---|---|
| 0 | 65 |
| 30 | 100 |
| 60 | 60 |
| 80 | 30 |

This indicates an overall temperature range of from 0° C. to about 80° C. Preferably, the range will be from about 10° C. to about 30° C. The time of reaction is not critical but if the temperature at this stage is allowed to rise substantially above the stated upper portion of the range, the product expected will not be obtained.

Following mixing molybdic oxide and the hydroxide an approximate amount, based on the hydroxide, of a strong mineral acid, such as sulfuric acid, can be used. Since this is normally used before the addition of the phosphorodithioic acid, the temperature of its addition and reaction should be kept within the stated range or the initial reaction mixture should be cooled prior to adding the dithioic acid.

In carrying out the reaction, there should be a 2:1 molar ratio of phosphorus acid to molybdate. Overall, this can range up to 5:1 to assure complete reaction of molybdate. The 2:1 ratio is preferred.

The amount of compound in the lubricant will usefully range from about 0.5% to about 10% by weight of said lubricant, preferably from about 1% to about 4% by weight.

The lubricants contemplated for use with the esters herein disclosed include both mineral and synthetic hydrocarbon oils of lubricating viscosity, mixtures thereof with other synthetic oils and the greases therefrom. The synthetic hydrocarbon oils include long chain alkanes such as cetanes and olefin polymers such as trimers and tetramers of octene and decene. The synthetic oils with which these can be mixed include (1) ester oils such as pentaerythritol esters of monocarboxylic acids having 2 to 20 carbon atoms, (2) polyglycol ethers, (3) polyacetals and (4) siloxane fluids. Especially useful among the synthetic esters are those made from polycarboxylic acids and monohydric alcohols. More preferred are the ester fluids made from pentaerythritol, or mixtures thereof with di- and tripentaerythritol, and an aliphatic monocarboxylic acid containing from 1 to 20 carbon atoms, or mixtures of such acids.

Having described the invention in general terms, the following are offered to specifically illustrate the development. It is to be understood they are illustrations only and that the invention shall not be limited except as limited by the appended claims.

EXAMPLE 1

Sodium hydroxide (0.060 mol., 4.84 g. of a 50% aqueous solution) was added to a slurry of molybdenum (VI) oxide (0.070 mol., 10.0 g.) in 15 ml. water, and the solution was heated to 80° C. with stirring until the molybdenum (VI) oxide dissolved. Sulfuric acid (0.028 mol., 2.92 g. of a 98% aqueous solution) was added, and the solution was allowed to cool to room temperature. While a slow stream of sulfur dioxide was passed through the solution, O,O-di(2-ethylhexyl)phosphorodithioic acid (0.138 mol., 49.0 g.) was added and the mixture was stirred at room temperature (25° C.) in a stream of sulfur dioxide (339 g. total) for five hours. The resulting maroon-colored organic phase was dissolved in hexane, separated, washed twice with water, and concentrated by vacuum rotary evaporation to give 55.8 g. of μ-oxo-bis[oxobis-(O,O-di-2-ethylhexyl phosphorothiolothionato) molybdenum (V)]. Phosphorus-31 NMR: $\delta P = 96.9$ ppm. Visible spectrum (isooctane) $\lambda max = 501$ nm.

Anal. Calcd. for $C_{64}H_{136}O_{11}Mo_2P_4S_8$: C, 46.47; H, 8.29; Mo, 11.60; P, 7.49; S. 15.51.

Found: C, 48.01; H, 8.52; Mo, 9.72; P, 7.15; S, 15.25.

EXAMPLE 2

The same procedure as Example 1 was used, except that the sulfur dioxide was omitted. The yield of μ-oxo-bis[oxobis-(O,O-di-2-ethylhexylphosphorothiolothionato)molybdenum(V)] was 55.4 g. Phosphorus-31 NMR spectrum, $\delta P = 97.0$ ppm, visible spectrum (isooctane), $\lambda max = 501$ nm.

Anal. Calcd. for $C_{64}H_{136}O_{11}Mo_2P_4S_8$: C, 46.47; H, 8.29; Mo, 11.60; P, 7.49; S, 15.51.

Found: C, 49.54; H, 8.69; Mo, 8.50; P, 7.44; S, 16.02.

EXAMPLE 3

μ-Oxo-bis[oxobis-(O,O-di-n-butylphosphorothiolothionato)molybdenum(V)] was prepared from O,O-di-n-butyl phosphorodithioic acid and ammonium heptamolybdate tetrahydrate in a stream of sulfur dioxide. To a solution of ammonium heptamolybdate tetrahydrate $((NH_4)_6Mo_7O_{24}.4H_2O$, 0.103 mol., 18.2g.) in water (25 ml.) was added O,O-di-n-butylphosphorodithioic acid (0.207 mol., 50 g.) while a stream of sulfur dioxide (43.4 g. total) was passed through the stirred solution. The reaction mixture was stirred five hours at 25° C. in the presence of a stream of sulfur dioxide (43.4 g. total). The reaction product was removed by filtration and washed to give 54.4 g. of crude product. Recrystallization from ethanol yielded 33.7 g. of pure μ-oxo-bis[oxobis-(O,O-di-n-butylphosphorothiolothionato)molybdenum(V)], violet crystals having a melting point of 118°–119° C. Phosphorus-31 NMR spectrum, $\delta P = 97.2$ ppm. Visible spectrum (isooctane) $\lambda max = 501$ nm.

Anal. Calcd. for $C_{32}H_{72}O_{11}Mo_2P_4S_8$: C, 31.89; H, 6.02; Mo, 15.92; P, 10.28; S, 21.28.

Found: C, 31.63; H, 6.10; Mo, 17.13; P, 11.39; S, 20.08.

EXAMPLE 4

μ-Oxo-bis[oxobis-(O,O-di-2-ethylhexylphosphorothiolothionato)molybdenum(V)] was prepared from O,O-di-2-ethylhexylphosphorodithioic acid (50.0 g.) and ammonium heptamolybdate tetrahydrate (12.44 g.) according to the procedure given in Example 1. The yield was 55.6 g. It had substantially the same analyses as Example 1.

EXAMPLE 5

μ-Oxo-bis[oxobis-(O,O-di-iso-propylphosphorothiolothionato)molybdenum(V)] was prepared according to the procedure described in Example 3, except that O,O-di(isopropyl)phosphorodithioic acid was the reactant. Phosphorus-31 NMR spectrum, $\delta P = 96.9$. Visible spectrum (isooctane) $\lambda max = 501$ nm.

Anal. Calcd. for $C_{24}H_{56}O_{11}Mo_2P_4S_8$:C, 26.37; H, 5.16; Mo, 17.56; P, 11.34; S, 23.47.

Found: C, 26.02; H, 5.32; Mo, 16.94; P, 11.30; S, 23.01.

EVALUATION OF THE PRODUCT

Low Velocity Friction Apparatus (LVFA)

The Low Velocity Friction Apparatus (LVFA) is used to measure the friction of test lubricants under various loads, temperatures, and sliding speeds. The LVFA consists of a flat SAE 1020 steel surface (diam. 1.5 in.) which is attached to a drive shaft and rotated over a stationary, raised, narrow ringed SAE 1020 steel surface (area 0.08 in.[2]). Both surfaces are submerged in the test lubricant. Friction between the steel surfaces is measured as a function of the sliding speed at a lubricant temperature of 250° F. The friction between the rubbing surfaces is measured using a torque-arm strain gauge system. The strain gauge output, which is calibrated to be equal to the coefficient of friction, is fed to the Y axis of an X-Y plotter. The speed signal from the tachometer-generator is fed to the X-axis. To minimize external friction, the piston is supported by an air bearing. The normal force loading the rubbing surfaces is regulated by air pressure on the bottom of the piston. The drive system consists of an infinitely variable-speed hydraulic transmission driven by a ½ HP electric motor. To vary the sliding speed, the output speed of the transmission is regulated by a lever-cammotor arrangement.

Procedure

The rubbing surfaces and 12-13 ml. of test lubricant are placed on the LVFA. A 500 psi. load is applied, and the sliding speed is maintained at 30 fpm at ambient temperature for a few minutes. A plot of coefficients of friction ($U_k$) over a range of sliding speeds, 5 to 40 fpm (25-195 rpm), is obtained. A minimum of three measurements is obtained for each test lubricant. Then, the test lubricant and specimens are heated to 250° F., another set of measurements is obtained, and the system is run for 50 minutes at 250° F., 500 psi, and 30 fpm sliding speed. Freshly polished steel specimens are used for each run. The surface of the steel is parallel ground to 15 to 20 microinches.

The data obtained are shown in Table 2.

TABLE 2

| Additive | Conc. % Wt. | % Change in Coeff. of Friction Relative to Base Oil[a][b] |
|---|---|---|
| 1 | 2 | 46 |
| 2 | 4 | 47 |

[a] The base oil is a lubricating oil comprising about 66% by weight of a synthetic hydrocarbon fluid (SHC) and about 20% by weight of an ester fluid. The SHC has a typical viscosity at 210° F. of about 7.0 cSt., and the ester fluid has a typical viscosity at 0° F. of 10.0 cSt. The percentages by weight are percentages by weight of the total lubricating oil composition, including the usual additive package.
[b] The data are percent decrease in friction according to:

$$\frac{(\text{Friction of oil alone}) - (\text{Friction of additive plus oil}) \times 100}{(\text{Friction of oil alone})}$$

Thus, the corresponding value for the oil alone would be zero for the form of the data used.

I claim:
1. A compound having the formula:

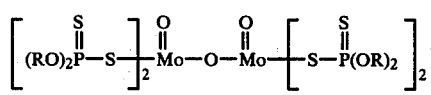

wherein R may be the same or different and is a $C_3$-$C_{30}$ hydrocarbyl group.

2. The compound of claim 1 wherein R is 2-ethylhexyl.
3. The compound of claim 1 wherein R is butyl.
4. The compound of claim 1 wherein R is n-butyl.
5. The compound of claim 1 wherein R is propyl.
6. The compound of claim 1 wherein R is iso-propyl.

7. A lubricant composition comprising a major proportion of a lubricant and a minor friction reducing amount of the compound of claim 1.
8. The composition of claim 7 wherein R is 2-ethylhexyl.
9. The composition of claim 7 wherein R is butyl.
10. The composition of claim 7 wherein R is n-butyl.
11. The composition of claim 7 wherein R is propyl.
12. The composition of claim 7 wherein R is iso-propyl.
13. A method for reducing fuel consumption in an internal combustion engine by treating the moving surfaces thereof with a composition comprising a major amount of a lubricating oil containing a fuel reducing amount of a compound of the formula:

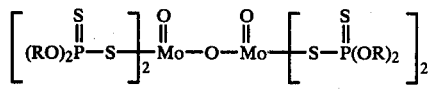

wherein R may be the same or different and is a $C_3$-$C_{30}$ hydrocarbyl group.

14. The composition of claim 13 wherein R is 2-ethylhexyl.
15. The composition of claim 13 wherein R is butyl.
16. The composition of claim 13 wherein R is n-butyl.
17. The composition of claim 13 wherein R is propyl.
18. The composition of claim 13 wherein R is iso-propyl.
19. A process for preparing a compound of the formula

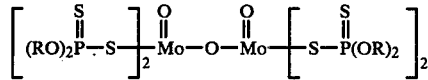

wherein R may be the same or different and is a $C_3$-$C_{30}$ hydrocarbyl group, comprising the step of reacting a metal molybdate or an ammonium molybdate with a dihydrocarbyl phosphorodithioic acid, the hydrocarbyl being as defined herein, at a temperature of no higher than about 80° C., the molar ratio of said molybdate to said acid being at least 1:2.
20. The process of claim 19 wherein the hydrocarbyl group is an alkyl, a cycloalkyl, an aryl or an alkaryl group.
21. The process of claim 19 wherein the temperature is from about 10° C. to about 30° C.
22. The composition of claim 19 wherein R is 2-ethylhexyl.
23. The composition of claim 19 wherein R is butyl.
24. The composition of claim 19 wherein R is n-butyl.
25. The composition of claim 19 wherein R is propyl.
26. The composition of claim 19 wherein R is iso-propyl.

* * * * *